United States Patent [19]

Meyers et al.

[11] Patent Number: 5,165,931

[45] Date of Patent: Nov. 24, 1992

[54] PEPTIFLUORIN AND NEOPEPTIFLUORIN

[75] Inventors: Edward Meyers, East Brunswick; Wen-Chih Liu, Princeton Junction; Gordon W. Robinson, Lawrenceville, all of N.J.

[73] Assignee: E. R. Squibb & Sons, Inc., Princeton, N.J.

[21] Appl. No.: 676,614

[22] Filed: Mar. 28, 1991

Related U.S. Application Data

[63] Continuation-in-part of Ser. No. 437,415, Nov. 15, 1989, abandoned.

[51] Int. Cl.$^5$ .............................................. A61K 35/74
[52] U.S. Cl. ................................................... 424/118
[58] Field of Search ........................................ 424/118

*Primary Examiner*—Jerome D. Goldberg
*Attorney, Agent, or Firm*—Theodore R. Furman, Jr.; Suzanne E. Babajko

[57] ABSTRACT

Two related, novel antibiotic substances, peptifluorin and neopeptifluorin, are prepared by cultivation of strains of *Pseudomonas fluorescens*, A. T. C. C. No. 53,958 and A. T. C. C. No. 55,129, respectively.

2 Claims, 6 Drawing Sheets

PEPTIFLUORIN AND NEOPEPTIFLUORIN

This is a continuation-in-part of U.S. Ser. No. 437,415 filed Nov. 15, 1989, now abandoned.

SUMMARY OF THE INVENTION

Cultivation of a strain of the microogranism, *Pseudomonas fluorescens,* that has been deposited in the American Type Culture Collection with the accession number, A.T.C.C. 53,958, yields the novel antibiotic substance peptifluorin, whereas cultivation of another isolate of *Pseudomonas fluorescens,* namely A.T.C.C. No. 55,129, yields the novel and related substance, neopeptifluorin. Both antibiotics possess broad spectrum antibacterial activity and antifungal activity.

DETAILED DESCRIPTION OF THE INVENTION

The Microorganisms

Figure 1:
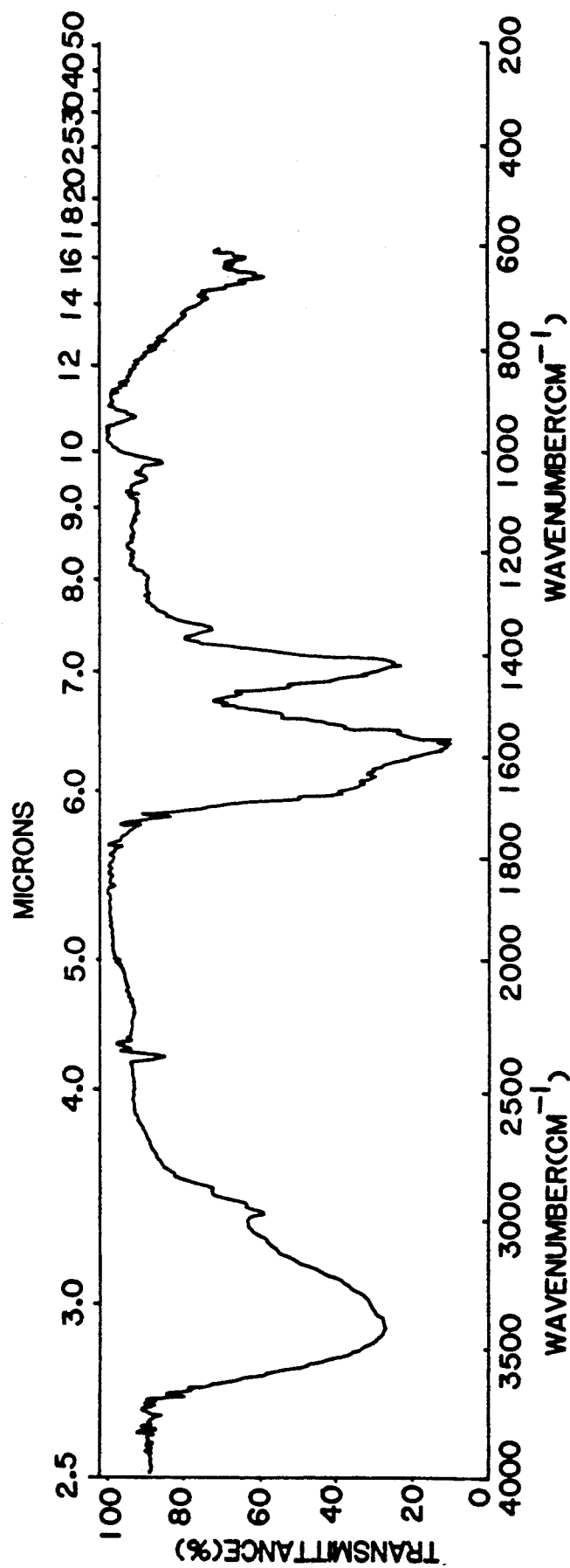
FIG. 1 shows the IR spectrum of peptifluorin in potassium bromide.

The microorganism used to produce peptifluorin was isolated from a sample of pond sediment. A subculture of the microorganism can be obtained from the permanent collection of the American Type Culture Collection, Rockville, Md. where its accession number is A.T.C.C. 53,958. In addition to the specific microorganism described and characterized herein, it should be understood that mutants (produced by the use of x-rays, mutagens, etc.) can also be cultivated to produce peptifluorin.

The microorganism used to produce neopeptifluorin was isolated from a sample of wet, decaying leaf litter. A subcultrue of the microorganism can be obtained from the permanent collection of the American Type Culture Collection, Rockville, Md., where its accession number is A.T.C.C. No. 55,129. In addition to the specific microorganism described and characterized herein, it should be understood that mutants (produced by the use of x-rays, mutagens, etc.) can also be cultivated to produce neopeptifluorin.

*Pseudomonas fluorescens,* A.T.C.C. No. 53,958, can be isolated from pond sediment in which it is present (in this instance obtained in Hamilton Township, N.J.) by first suspending the sample in sterile diluent (e.g., buffered saline containing 0.01% gelatin) and shaking. A dilution of this suspension is plated onto a nutrient medium that has been supplemented with cycloheximide. The composition of this medium is:

| | Grams |
|---|---|
| Yeast extract | 0.4 |
| Mannitol | 10.0 |
| Potassium Hydrogen Phosphate, Dibasic | 0.5 |
| Sodium Chloride | 0.1 |
| Magnesium Sulfate Septahydrate | 0.2 |
| Agar | 15.0 |
| Congo red | 10.0 ml of a 0.25% aqueous solution |
| Distilled water | 800 ml |
| Cycloheximide* | 10 ml of a 1% aqueous solution |

*Filter sterilized and added to the medium that has already been adjusted to pH about 6.8 and sterilized by autoclaving at 121° C. for 30 minutes.

After 3 days incubation at room temperature, the colonies of *Pseudomonas fluorescens,* A.T.C.C. No. 53,958, are isolated from the plated sediment and are picked off and maintained on Nutrient Agar (Difco Labs., Detroit Mich.).

The organism is a gram negative, motile rod occurring singly or as short, plump diplobacilli. It is motile by means of one or more polar flagella. The organism exists in rough and smooth colony types, both of which exhibit the same biochemical characteristics. The organism is oxidative on Hugh Leifson's O/F glucose test, is cytochrome oxidase positive and is fluorescent on King's B medium. No pyocyanin pigment is produced on King's A medium and no diffusible pigments are noted.

The following biochemical reactions are positive: catalase, arginine dihydrolase, gelatinase. The following biochemical reactions are negative: starch hydrolysis, nitrate reduction, indole, poly β-hydroxybutyrate.

The following compounds can be utilized as sole carbon sources: DL-arginine, citrate, glucose, xylose and sucrose.

Growth of the organism occurs at 4° C. but not at 42° C.

These characteristics agree with those of *Pseudomonas fluorescens* and serve to identify the producer of peptifluorin as *Pseudomonas fluorescens.*

*Pseudomonas fluorescens,* A.T.C.C. No. 55,129, can be isolated from wet, decaying leaf litter in which it is present (in this instance obtained in Veteran's Park, Hamilton Township, N.J.) in a manner identical to that described for the isolation of *Pseudomonas fluorescens,* A.T.C.C. No. 53,958. The morphological, staining and biochemical characteristics of this organism are in agreement with those described above for *Pseudomonas fluorescens* and therefore serve to identify the producer of neopeptifluorin as *Pseudomonas fluorescens.*

The Antibiotics

The antibiotic peptifluorin can be produced by cultivating *Pseudomonas fluorescens,* A.T.C.C. No. 53,958, at, or about, room temperature (25° C.) under submerged aerobic conditions in an aqueous nutrient medium containing an assimilable source of carbon and an assimilable source of nitrogen. The fermentation is carried out until substantial antibiotic activity is imparted to the medium, usually about 24 to 48 hours. The fermentation, as well as subsequent isolation steps, can be monitored by means of a conventional paper disc-agar diffusion assay with *Staphylococcus aureus* as the assay organism. Peptifluorin can be isolated and purified by art-recognized techniques from the broth supernatant, after removal of the cell mass by centrifugation.

To obtain the antibiotic from the fermentation supernatant, the antibiotic is sorbed onto the non-ionic resin, XAD-2, and subsequently eluted with methanol. The active methanol eluate is treated further by chromatography on CHP20P from which the activity is eluted with a solvent having a linear gradient from acetonitrile-water-trifluoroacetic acid: 200:800:1 to 800:200:1. The active fractions are pooled and purified further by treatment with a 1:1 mixture of Darco G60 charcoal and celite filter aid, and subsequent filtration and washing with acetonitrile:water, 20:80 and 30:70 and recovery of the activity in the combined filtrate and washings.

Alternatively, the activity can be recovered from the fermentation supernatant by extraction into n-butanol followed by concentration of the organic layer in vacuo and subsequent sorption of the concentrate onto the non-ionic resin, XAD-2. Further purification is effected as described above for processing the activity in the supernatant fraction.

Neopeptifluorin can be produced by cultivating *Pseudomonas fluorescens*, A.T.C.C. No. 55,129, in the same manner as described for peptifluorin and isolated and purified by the same art-recognized techniques described for the isolation and purification of peptifluorin.

The following examples further illustrate these inventions.

EXAMPLE 1

Preparation of Peptifluorin

Nutrient agar slants were seeded with *Pseudomonas fluorescens*, A.T.C.C. No. 53,958, and incubated overnight at 25° C. The subsequent growth was used to inoculate 50 ml portions of an aqueous medium contained in 250 ml Erlenmeyer flasks. The composition of the germination medium was:

| | |
|---|---|
| Yeast extract | 5.0 g |
| Peptone | 3.0 g |
| Mannitol | 5.0 g |
| Distilled water to | 1000 mL. |

The medium was sterilized at 121° C. for 15 minutes prior to use.

The inoculated germination flasks were incubated at 25° C. on a rotary shaker for about 24 hours. The shaker operated at a speed of 300 rpm with a 2-inch stroke. At that time, a 1% transfer was made from the growth in the germination flasks to fresh, 50 ml portions of the same medium in 250 ml Erlenmeyer flasks. The inoculated flasks were incubated at 25° C. for about 24 hours on a rotary shaker operating at 300 rpm with a 2-inch stroke.

At harvest, the pooled contents of the flasks were centrifuged to separate supernatant and solids. The solids were discarded. About 0.9 L of XAD-2 resin was added to a 10-L portion of the supernatant and the suspension, adjusted to pH 7, was mixed gently on a rotary mixer for 15 minutes. The chargd resin was then separated and washed with water (6 L) followed by methanol:water, 1:1 (6 L). The activity was eluted with methanol (3 L) and the active eluate concentrated in vacuo to yield 0.83 g of crude peptifluorin. This procedure was repeated with other 10-L portions of fermentation supernatant until 1.7 g of crude antibiotic was accumulated. A 1.6-g sample of the crude antibiotic, dissolved in 10 mL of acetonitrile:water:trifluoroacetic acid, 200:800:1, was applied to a column (5×41 cm) of CHP20P resin, packed in the same solvent. The antibiotic was eluted with a linear gradient of acetonitrile:water:trifluoroacetic acid, 200:800:1 to 800:200:1 over 3600 mL, at a flow rate of 9 mL/minute, collecting 23 mL fractions. The pooled, active fractions were concentrated in vacuo to an aqueous solution and lyophilized to yield enriched peptifluorin, 0.61 g. This material was dissolved in 10 mL of acetonitrile:water, 20:80, and further purified by treatment with 15 mL of a 1:1 mixture of Darco G60 charcoal:celite filter aid that had been washed with a mixture of acetonitrile:water: trifluoroacetic acid, 500:500:1, followed by water until neutrality. The mixture was filtered and the solids were washed with 50 mL of acetonitrile: water, 20:80, and 80 mL of the same solvents in a 30:70 mixture. The combined filtrate and washings were concentrated in vacuo to an aqueous solution that was lyophilized to yield purified peptifluorin, 0.39 g.

EXAMPLE 2

Preparation of Neopeptifluorin

The production and isolation of neopeptifluorin was accomplished in a manner similar to that used for the isolatin of peptifluorin. The fermentation media and conditions for the production of neopeptifluorin were identical to those described for the production of peptifluorin except that *Pseudomonas fluorescens*, A.T.C.C. No. 55,129, was used. At the completion of the fermentation, two 10 L portions of broth supernatant were treated with XAD-2 resin as described above to yield the active methanol eluates. These were combined to yield 1.78 g of crude neopeptifluorin. This material (1.45 g) was dissolved in 30 mL of acetonitrile:water:trifluoroacetic acid, 200:800:1, and applied to a column (5×27 cm) of CHP20P resin packed in the same solvent. After washing the resin with 750 ml of this same solvent, the activity was eluted with 750 mL of acetonitrile:water:trifluoroacetic acid, 350:650:1 and 750 ml of 500:500:1 solvent mixture. The active eluates were combined and concentrated in vacuo to an aqueous solution that was lyophilized to yield 0.62 g of enriched neopeptifluorin. A 0.60 g sample of enriched neopeptifluorin was further purified by treatment with Darco G60 charcoal, according to the procedure described for the purification of peptifluorin, giving 0.162 g of purified neopeptifluorin.

Figure 2:
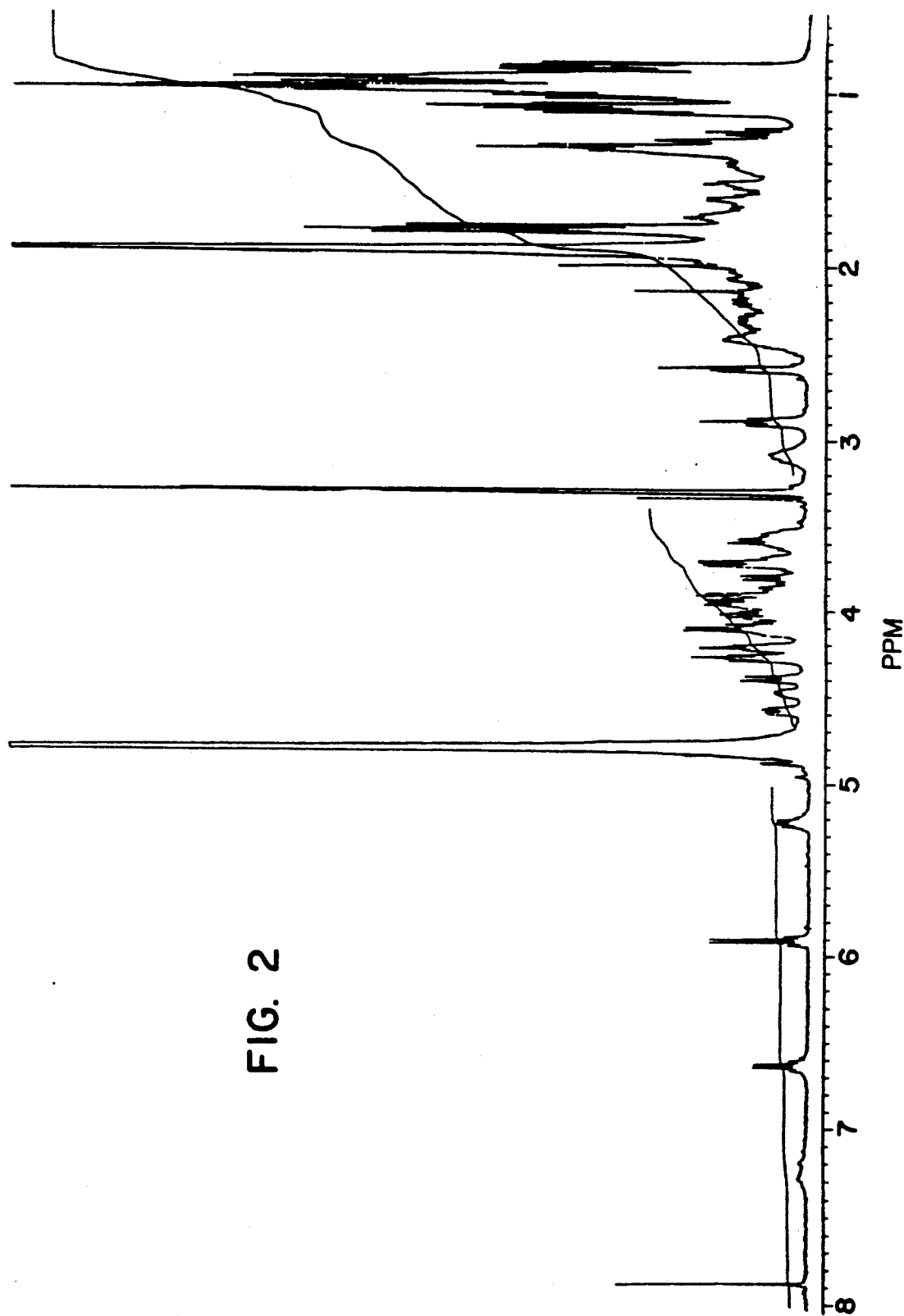
FIG. 2 shows the 400 MHz $^1$H NMR spectrum of peptifluorin in CD$_3$OD.
Figure 3:
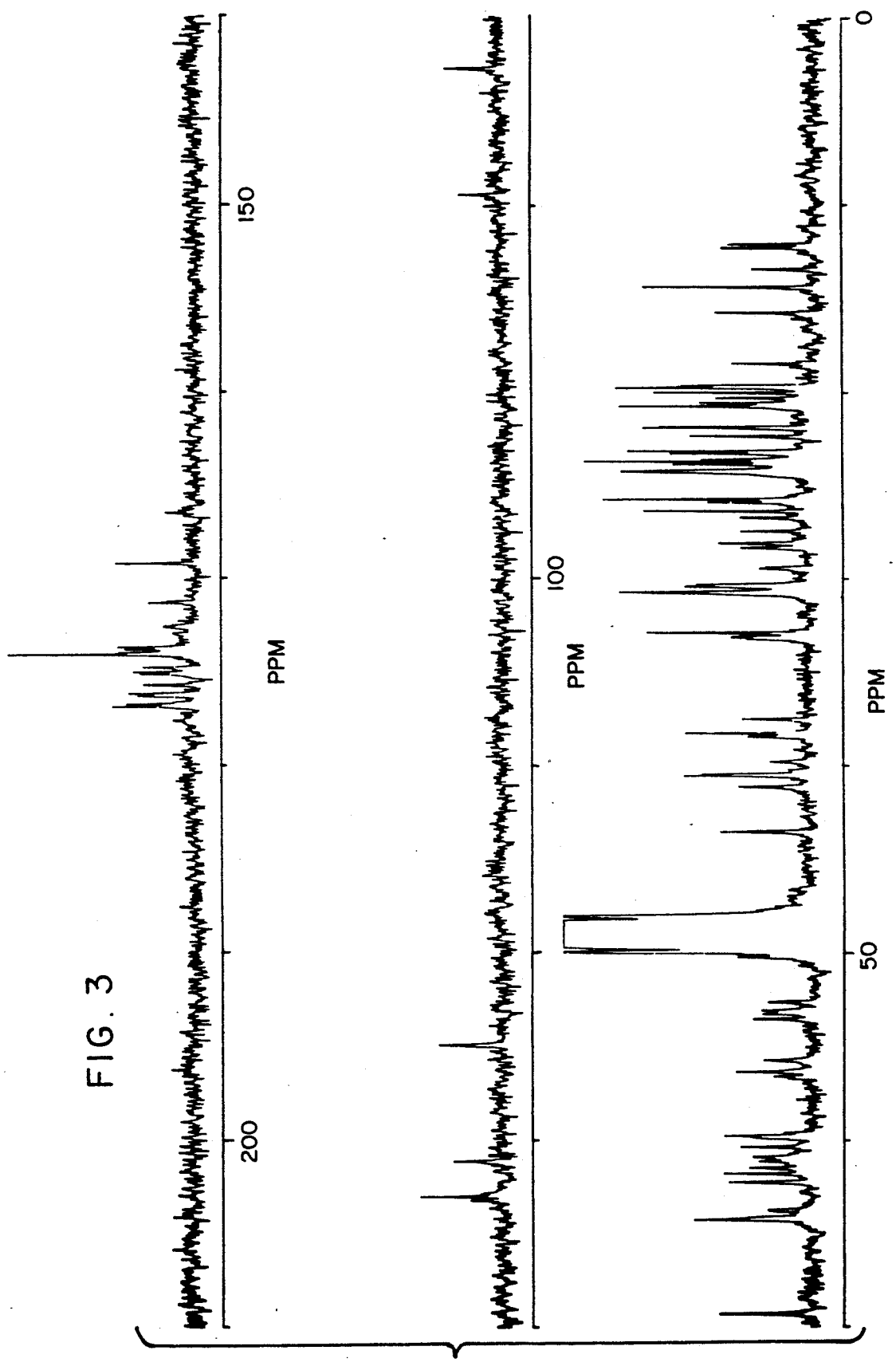
FIG. 3 shows the 67.5 MHz $^{13}$C NMR spectrum of peptifluorin in CD$_3$OD.

Peptifluorin has the following characteristics: the fast atom bombardment mass spectra (FAB-MS) have peaks at m/z 1987 in the positive ion mode and at 1985 in the negative ion mode, for a nominal molecular weight of 1986; UVmax (methanol) end absorption; IR (potassium bromide) as shown in FIG. 1; 400 MHz $^1$H NMR spectrum in $CD_3OD$ as shown in FIG. 2; 67.5 MHz $^{13}$C NMR spectrum in $CD_3OD$ as shown in FIG. 3; the electrophoretic mobility of peptifluorin on paper relative to vitamin $B_{12}$ (0.0) and the p-nitrobenzenesulfonate anion (1.0) when using a buffer consisting of formic acid, acetic acid and water, 1:3:36 is 0.45 and is 0.25 when using 0.05M potassium hydrogen phosphate buffer; melting point of 225°-230° C.; peptifluorin gives positive ninhydrin (purple) and Rydon-Smith color reactions; elemental analysis 47.93% C; 7.40% H; 10.10% N.

These characteristics serve to distinguish peptifluorin from all known antibiotics.

Figure 4:
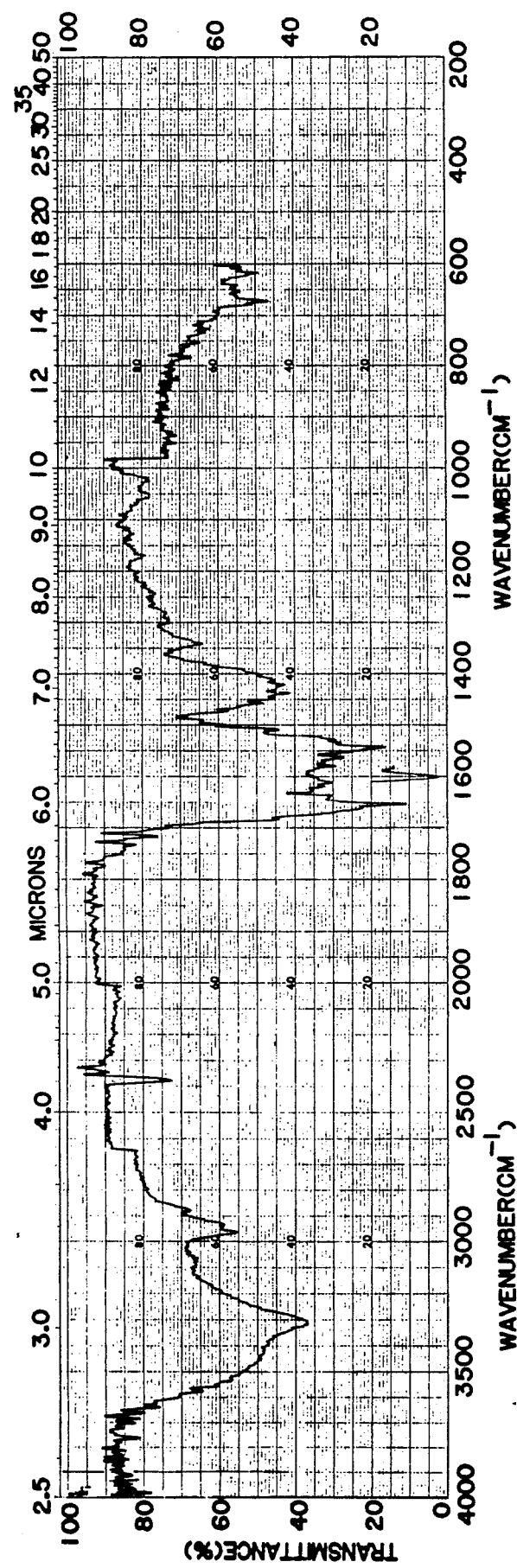
FIG. 4 shows the IR spectrum of neopeptifluorin in potassium bromide.
Figure 5:
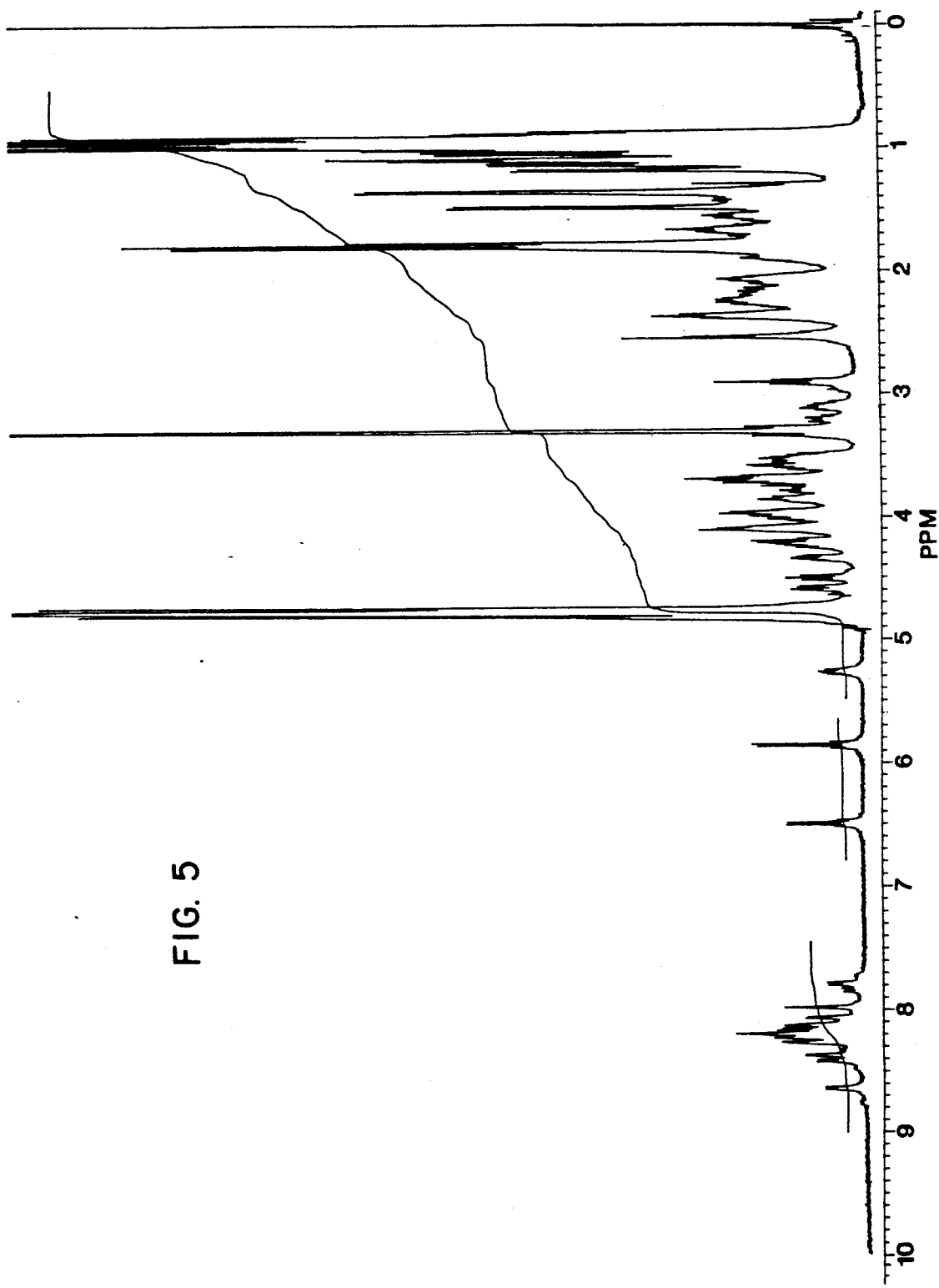
FIG. 5 shows the 400 MHz $^1$H NMR spectrum of neopeptifluorin in CD$_3$OD.
Figure 6:
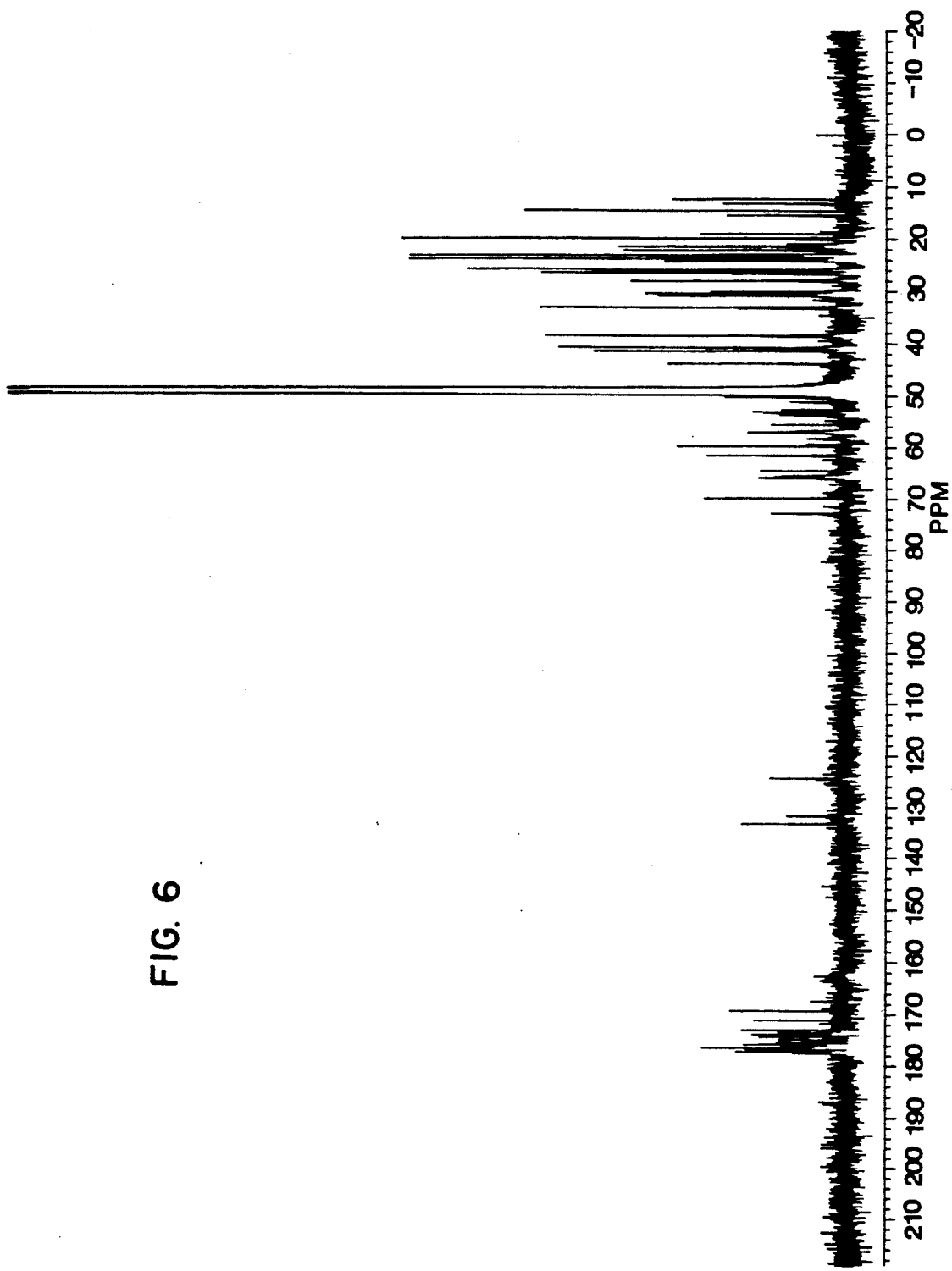
FIG. 6 shows the 67.5 MHz $^{13}$C NMR spectrum of neopeptifluorin in CD$_3$OD.

Neopeptifluorin has the following characteristics: the fast atom bombardment mass spectra (FAB-MS) have peaks at m/z 1971 in the positive ion mode and at 1969 in the negative ion mode, for a nominal molecular weight of 1970; UVmax (methanol) end absorption; IR (potassium bromide) as shown in FIG. 4; 400 MHz $^1$H NMR spectrum in CD$_3$OD as shown in FIG. 5; 67.5 MHz $^{13}$C NMR spectrum in CD$_3$OD as shown in FIG. 6; the electrophoretic mobility of neopeptifluorin on paper relative to vitamin B$_{12}$ (0.0) and the p-nitrobenzenesulfonate anion (1.0) is the same as that given for peptifluorin in the buffer systems reported for peptifluorin; melting point of >300° C.; neopeptifluorin gives positive ninhydrin (purple) and Rydon-Smith color reactions; elemental analysis 47.05% C; 7.00% H; 9.30% N.

In addition to the characteristics above, the following amino acids were obtained upon hydrolysis of peptifluorin with 6N HCl at 110° C. for 24 to 48 hours; D-Glu (1), D-Ser (2), Pro (1), Dab (1), homoserine (2), D-Val (2), L-Val (1), L-Ile (0~1), D-Leu (2), L-Leu (1), L-Lys (1), Abu (2). For neopeptifluorin, the following amino acids were obtained: Glu (1), Ser (1), Ala (1), Pro (1), Dab (1), homoserine (2), Val (3), Leu (3~4), Lys (1), -Abu (2).

These characteristics serve to distinguish peptifluorin from neopeptifluorin and both from all known antibiotics.

BIOLOGICAL ACTIVITY

The following methodology was used to determine the minimum inhibitory concentration (hereinafter referred to as MIC) of the compound of this invention against bacteria. The test organisms were grown in 20 ml of Antibiotic Assay Broth (Difco) by inoculating the broth (in tubes) with a loopful of the organism from a BHI (Difco) agar slant. The inoculated tubes were incubated at 37° C. for 18 to 24 hours. These cultures were assumed to contain 10$^9$ colony forming units (CFU) per ml. The cultures were diluted 1:100 to give a final inoculum level of 10$^7$ CFU; dilutions were made with Yeast Beef Broth (Difco). The test compound was dissolved in an appropriate diluent at a concentration of 1,000 μg/ml. Two-fold dilutions were made in Yeast Beef Broth (Difco), resulting in a range from 1000 μg/ml to 0.5 μg/ml. A 1.5 ml portion of each dilution was placed into individual petri dishes to which 13.5 ml of K-10 agar was added. The composition of K-10 agar is:

| Beef extract | 1.5 g |
|---|---|
| Yeast extract | 3.0 g |
| Peptone | 6.0 g |
| Dextrose | 1.0 g |
| Agar | 15.0 g |
| Distilled water | q.s. to 1000 ml |

The medium was sterilized at 121° C. for 15 minutes at 15 pounds psi.

The final drug concentration in the agar ranged from 100 μg/ml to 0.05 μg/ml. Organism growth control plates containing agar only were prepared and inoculated before and after the test plates. The organisms were applied to the agar surface of each plate with a Denly Multipoint Inoculator (which delivers approximately 0.001 ml of each inoculum) resulting in a final inoculum of 10$^4$ CFU on the agar surface.

The plates were incubated at 37° C. for 18 hours and the MICs determined. The MIC is the lowest concentration of compound inhibiting growth of the organism.

The methodology described above was modified in the assay for activity against yeasts. Fresh F-4 slants of the test organisms were obtained from frozen vials (−70° C.). The cultures were inoculated into tubes of F-4 broth and incubated at 37° C. for 18 to 24 hours, at which time the average cell count was assumed to be 5×10$^7$ CFU per ml. These were diluted 1:50 with fresh F-4 broth to give an inoculum level of 1×10$^6$ CFU per mL. The organisms were then dispensed into a sterile template (0.8 ml per well) and delivered onto the surface of each plate containing test compound as described above with a Denly Multipoint Inoculator, resulting in a final inoculum of 10$^3$ CFU on the agar surface.

The composition of the F-4 broth is:

| Tryptone | 5 g |
|---|---|
| Malt extract | 3 g |
| Glucose | 10 g |
| Yeast Extract | 3 g |
| Distilled water to | 1000 ml. |

The medium was sterilized at 121° C. for 15 minutes at 15 psi.

F-4 agar has the same composition as the broth but with the addition of 15 g agar per liter.

The results of the agar dilution assays with bacteria are:

| PEPTIFLUORIN | | |
|---|---|---|
| Organism | | MIC (μg/mL) |
| Staphylococcus aureus | SC 1276* | 6.3 |
| Staphylococcus aureus | SC 2399 | 6.3 |
| Staphylococcus aureus | SC 2400 | 6.3 |
| Streptococcus faecalis | SC 9011 | 6.3 |
| Micrococcus luteus | SC 2495 | 6.3 |
| Escherichia coli | SC 8294 | >100.0 |
| Escherichia coli | SC 10,896 | 12.5 |
| Escherichia coli | SC 10,857 | 50.0 |
| Klebsiella pneumoniae | SC 10,440 | 50.0 |
| Klebsiella pneumoniae | SC 9527* | >100.0 |
| Salmonella typhosa | SC 1195 | >100.0 |
| Shigella sonnei | SC 8449 | 25.0 |
| Enterobacter cloacae | SC 8236 | 25.0 |

*SC denotes organisms from the general culture collection of E. R. Squibb & Sons, Inc.

| NEOPEPTIFLUORIN | | |
|---|---|---|
| Organism | | MIC (μg/mL) |
| Staphylococcus aureus | SC 1276* | 3.1 |
| Staphylococcus aureus | SC 2399 | 6.3 |
| Staphylococcus aureus | SC 2400 | 6.3 |
| Streptococcus faecalis | SC 9011 | 6.3 |
| Streptococcus agalactiae | SC 14,008 | 6.3 |
| Micrococcus luteus | SC 2495 | 6.3 |
| Escherichia coli | SC 8294 | 50.0 |
| Escherichia coli | SC 10,896 | 12.5 |
| Escherichia coli | SC 10,857 | 12.5 |
| Klebsiella pneumoniae | SC 10,440 | 25.0 |
| Klebsiella pneumoniae | SC 9527 | >100 |
| Salmonella typhosa | SC 1195 | 100 |
| Shigella sonnei | SC 8449 | 25 |
| Enterobacter cloacae | SC 8236 | 12.5 |

*SC denotes organisms from the general culture collection of E. R. Squibb & Sons, Inc.

The results of the yeast, agar dilution assays (determined after incubation at 37° C. for 36–48 hours) are:

| PEPTIFLUORIN | | |
|---|---|---|
| Organism | | MIC (μg/mL) |
| Candida albicans | SC 5314* | 12.5 |
| Candida albicans | SC 9177 | 25.0 |
| Candida albicans | SC 11,422 | 12.5 |
| Candida tropicalis | SC 8159 | 12.5 |
| Candida tropicalis | SC 9861 | 3.1 |
| Candida krusei | SC 2967 | 100 |
| Candida glabrata | SC 11,267 | 12.5 |
| Saccharomyces cerevisiae | SC 12,955 | 25.0 |
| Saccharomyces cerevisiae | SGY 1139** | 3.1 |
| Saccharomyces cerevisiae | SC 1600 | 12.5 |

*SC denotes organisms from the general culture collection of E. R. Squibb & Sons, Inc.
**SGY denotes organisms from the Yeast Genetics culture collection of Bristol-Myers Squibb, Inc.

| NEOPEPTIFLUORIN | | |
|---|---|---|
| Organism | | MIC (μg/mL) |
| Candida albicans | SC 5314* | 6.3 |
| Candida albicans | SC 9177 | 25.0 |
| Candida albicans | SC 11,422 | 12.5 |
| Candida tropicalis | SC 8159 | 6.3 |
| Candida tropicalis | SC 9861 | 3.1 |
| Candida krusei | SC 2967 | 100 |
| Candida glabrata | SC 11,267* | 25.0 |
| Saccharomyces cerevisiae | SC 12,955 | 12.5 |
| Saccharomyces cerevisiae | SGY 1139** | 1.6 |
| Saccharomyces cerevisiae | SC 1600 | 6.3 |

*SC denotes organisms from the general culture collection of E. R. Squibb & Sons, Inc.
**SGY denotes organisms from the Yeast Genetics culture collection of Bristol-Myers Squibb, Inc.

Both peptifluorin and neopeptifluorin, in addition to their antimicrobial activity, are moderately active in inhibiting mevalonate kinase from yeast, an enzyme involved in ergosterol biosynthesis in yeast.

What is claimed is:

1. Peptifluorin, having the infra-red absorption in potassium bromide as shown in FIG. 1, having the 400 MHz $^1$H NMR spectrum in CD$_3$OD as shown in FIG. 2, and having the 67.5 MHz $^{13}$C NMR spectrum in CD$_3$OD as shown in FIG. 3 and wherein the fast atom bombardment mass spectra has peaks at m/z 1987 in the positive ion mode and at 1985 in the negative ion mode for a nominal molecular weight of 1986, and having as an approximate elemental analysis, 47.93 percent carbon, 7.40 percent hydrogen, and 10.10 percent nitrogen.

2. Neopeptifluorin having the 67.5 MHz $^{13}$C NMR spectrum of neopeptifluorin in CD$_3$OD as shown in FIG. 6, having the 400 MHz $^1$H NMR spectrum of neopeptifluorin in CD$_3$OD as shown in FIG. 5, having the IR spectrum of neopeptifluorin in potassium bromide as shown in FIG. 4, and wherein the fast atom bombardment mass spectra has peaks at m/z 1971 in the positive ion mode and at 1969 in the negative ion mode for a nominal molecular weight of 1970, and having as an approximate elemental analysis, 47.05 percent carbon, 7.00 percent hydrogen, and 9.30 percent nitrogen.

* * * * *